(12) United States Patent
Wyeth et al.

(10) Patent No.: US 7,957,815 B2
(45) Date of Patent: Jun. 7, 2011

(54) ELECTRODE ASSEMBLY AND HANDPIECE WITH ADJUSTABLE SYSTEM IMPEDANCE, AND METHODS OF OPERATING AN ENERGY-BASED MEDICAL SYSTEM TO TREAT TISSUE

(75) Inventors: Richard Wyeth, Discovery Bay, CA (US); Bader-Eddine Bellahsene, San Mateo, CA (US); Mark L. Kane, San Jose, CA (US)

(73) Assignee: Thermage, Inc., Hayward, CA (US)

( * ) Notice: Subject to any disclaimer, the term of this patent is extended or adjusted under 35 U.S.C. 154(b) by 1286 days.

(21) Appl. No.: 11/537,155

(22) Filed: Sep. 29, 2006

(65) Prior Publication Data
US 2007/0083247 A1    Apr. 12, 2007

Related U.S. Application Data

(60) Provisional application No. 60/725,490, filed on Oct. 11, 2005.

(51) Int. Cl.
*A61F 7/00* (2006.01)
(52) U.S. Cl. .............................. 607/99; 607/96
(58) Field of Classification Search .............. 606/27–52; 607/97–99, 101–102
See application file for complete search history.

(56) References Cited

U.S. PATENT DOCUMENTS

| | | | |
|---|---|---|---|
| 3,870,047 A * | 3/1975 | Gonser | 606/45 |
| 4,304,235 A | 12/1981 | Kaufman | |
| 4,658,819 A | 4/1987 | Harris et al. | |
| 4,934,365 A | 6/1990 | Morgenthaler | |
| 5,281,216 A * | 1/1994 | Klicek | 606/42 |
| 5,487,759 A | 1/1996 | Bastyr et al. | |
| 5,660,836 A | 8/1997 | Knowlton | |
| 5,702,387 A | 12/1997 | Arts et al. | |
| 5,718,719 A | 2/1998 | Clare et al. | |
| 5,755,753 A | 5/1998 | Knowlton | |
| 5,849,020 A | 12/1998 | Long et al. | |
| 5,871,524 A | 2/1999 | Knowlton | |
| 5,919,219 A | 7/1999 | Knowlton | |
| 5,948,011 A | 9/1999 | Knowlton | |
| 6,148,232 A | 11/2000 | Avrahami | |
| 6,241,753 B1 | 6/2001 | Knowlton | |
| 6,293,941 B1 | 9/2001 | Strul et al. | |

(Continued)

FOREIGN PATENT DOCUMENTS
EP     1685805 A1    8/2006
(Continued)

OTHER PUBLICATIONS

U.S. Patent and Trademark Office, final Office Action issued in related U.S. Appl. No. 11/423,068 dated Apr. 2, 2010.

(Continued)

*Primary Examiner* — Roy D Gibson
(74) *Attorney, Agent, or Firm* — Wood, Herron & Evans, LLP (57) ABSTRACT

Electrode assemblies and handpieces for energy-based treatment systems that utilize an impedance assembly to facilitate impedance matching between the system and a patient. The electrode assembly and/or handpiece may include one or more circuit elements configured to introduce at least one supplemental impedance into an electrical circuit coupling the electrode assembly and handpiece. The supplemental impedance, which is related to the impedance of the treatment system and patient, is introduced when the electrode assembly is coupled with the handpiece.

47 Claims, 5 Drawing Sheets

U.S. PATENT DOCUMENTS

| | | | |
|---|---|---|---|
| 6,311,090 B1 | 10/2001 | Knowlton | |
| 6,325,799 B1 * | 12/2001 | Goble | 606/41 |
| 6,350,276 B1 | 2/2002 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | |
| 6,423,057 B1 | 7/2002 | He et al. | |
| 6,425,912 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,378 B1 | 10/2002 | Knowlton | |
| 6,470,216 B1 | 10/2002 | Knowlton | |
| 6,597,946 B2 | 7/2003 | Avrahami et al. | |
| 6,611,706 B2 | 8/2003 | Avrahami et al. | |
| 6,615,079 B1 | 9/2003 | Avrahami | |
| 6,696,844 B2 | 2/2004 | Wong et al. | |
| 6,708,060 B1 | 3/2004 | Avrahami et al. | |
| 6,711,435 B2 | 3/2004 | Avrahami | |
| 6,997,923 B2 | 2/2006 | Anderson et al. | |
| 7,006,874 B2 | 2/2006 | Knowlton et al. | |
| 7,022,121 B2 | 4/2006 | Stern et al. | |
| 7,062,317 B2 | 6/2006 | Avrahami et al. | |
| 7,094,215 B2 | 8/2006 | Davison et al. | |
| 7,115,123 B2 | 10/2006 | Knowlton et al. | |
| 7,123,957 B2 | 10/2006 | Avrahami | |
| 7,141,049 B2 | 11/2006 | Stern et al. | |
| 7,189,230 B2 | 3/2007 | Knowlton | |
| D544,955 S | 6/2007 | Carson et al. | |
| 7,229,436 B2 | 6/2007 | Stern et al. | |
| 7,257,450 B2 | 8/2007 | Auth et al. | |
| 7,267,675 B2 | 9/2007 | Stern et al. | |
| 7,276,058 B2 | 10/2007 | Altshuler et al. | |
| 7,351,252 B2 | 4/2008 | Altshuler et al. | |
| 7,452,358 B2 | 11/2008 | Stern et al. | |
| 7,473,251 B2 | 1/2009 | Knowlton et al. | |
| 7,473,252 B2 | 1/2009 | Barry | |
| 7,481,809 B2 | 1/2009 | Stern et al. | |
| 7,494,488 B2 | 2/2009 | Weber | |
| 2003/0163178 A1 | 8/2003 | Davison et al. | |
| 2003/0199868 A1 | 10/2003 | Desai et al. | |
| 2003/0208152 A1 | 11/2003 | Avrahami et al. | |
| 2003/0216719 A1 | 11/2003 | Debenedictis et al. | |
| 2003/0236487 A1 | 12/2003 | Knowlton | |
| 2004/0006339 A1 | 1/2004 | Underwood et al. | |
| 2004/0082940 A1 | 4/2004 | Black et al. | |
| 2004/0111087 A1 | 6/2004 | Stern et al. | |
| 2004/0210214 A1 | 10/2004 | Knowlton | |
| 2004/0230227 A1 | 11/2004 | Avrahami et al. | |
| 2005/0049582 A1 | 3/2005 | DeBenedictis et al. | |
| 2006/0122668 A1 | 6/2006 | Anderson et al. | |
| 2006/0206103 A1 | 9/2006 | Altshuler et al. | |
| 2007/0088413 A1 | 4/2007 | Weber et al. | |
| 2007/0093797 A1 | 4/2007 | Chan et al. | |
| 2007/0093798 A1 | 4/2007 | DeBenedictis et al. | |
| 2007/0093978 A1 | 4/2007 | Walling et al. | |
| 2008/0058782 A1 | 3/2008 | Frangineas et al. | |

FOREIGN PATENT DOCUMENTS

| | | |
|---|---|---|
| WO | 9639087 A1 | 6/1996 |
| WO | 9724073 A1 | 7/1997 |
| WO | 9912489 A2 | 3/1999 |
| WO | 9916502 | 4/1999 |
| WO | 0048644 A2 | 8/2000 |
| WO | 0053113 | 9/2000 |
| WO | 0100269 | 1/2001 |
| WO | 02053050 A1 | 7/2002 |
| WO | 03053266 | 3/2003 |
| WO | 03065905 A1 | 8/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |
| WO | 2005096979 A1 | 10/2005 |
| WO | 2005096980 A1 | 10/2005 |
| WO | 2007030415 A2 | 3/2007 |
| WO | 2007041540 A1 | 4/2007 |
| WO | 2007046886 A1 | 4/2007 |
| WO | 2007047122 A2 | 4/2007 |
| WO | 2008091983 A2 | 7/2008 |

OTHER PUBLICATIONS

European Patent Office, International Search Report issued in corresponding PCT Application serial No. PCT/US2006/038894 dated May 31, 2007.

U.S. Patent and Trademark Office, Office Action issued in related U.S. Appl. No. 11/423,068.

European Patent Office, International Search Report issued in corresponding PCT Application serial No. PCT/US2008/069647 dated Oct. 6, 2008.

European Patent Office, International Search Report issued in corresponding PCT Application serial No. PCT/US2008/051868 dated Jul. 3, 2008.

European Patent Office, International Search Report issued in corresponding PCT Application serial No. PCT/US2008/051868 dated Sep. 4, 2008.

European Patent Office, International Search Report issued in corresponding PCT Application serial No. PCT/US2006/038536 dated Jan. 23, 2007.

European Patent Office, International Search Report issued in corresponding PCT Application serial No. PCT/US2006/022586 dated Dec. 1, 2006.

Bryan Weber et al, "Treatment Apparatus and Methods for Inducing Microburn Patterns in Tissue", U.S. Appl. No. 12/019,874, filed Jan. 25, 2008.

Burns et al, "Treatment Apparatus and Methods for Delivering High Frequency Energy Across Large Tissue Areas", U.S. Appl. No. 12/171,010, filed Jul. 10, 2008.

Bryan Weber et al, Treatment Apparatus and Methods for Delivering Energy at Multiple Selectable Depths in Tissue, U.S. Appl. No. 11/423,068, filed Jun. 8, 2006.

Bryan Weber et al, Method and Apparatus for Estimating a Local Impedance Factor, U.S. Appl. No. 11/470,041, filed Sep. 5, 2006.

* cited by examiner

ELECTRODE ASSEMBLY AND HANDPIECE WITH ADJUSTABLE SYSTEM IMPEDANCE, AND METHODS OF OPERATING AN ENERGY-BASED MEDICAL SYSTEM TO TREAT TISSUE

CROSS-REFERENCE TO RELATED APPLICATIONS

This application claims the benefit of U.S. Provisional Application No. 60/725,490 filed Oct. 11, 2005, the disclosure of which is hereby incorporated by reference herein in its entirety.

FIELD OF THE INVENTION

The invention relates to energy-based medical systems of the type used for cosmetic or therapeutic treatment and, more particularly, to electrode assemblies and handpieces forming components of energy-based medical systems, and methods of operating an energy-based medical system to treat tissue.

BACKGROUND OF THE INVENTION

Energy-based medical systems are often utilized to treat patients for various medical, cosmetic, and therapeutic reasons. For example, energy-based treatment systems may be utilized to heat selected areas and portions of a patient's tissue by applying energy to the tissue. Controlled heating of tissue often produces various beneficial effects, including improving the appearance of skin by removing or reducing wrinkles, tightening skin, removing unwanted hair, etc. Energy-based systems generate a signal, such as a radiofrequency (RF) signal, that is then applied to the patient. Generation of signals and delivery of these signals is often performed by a radiofrequency generator. To achieve optimum and desired energy delivery efficiencies, the output impedance of the radiofrequency generator's signal may be tailored to match the patient tissue load impedance. By definition, an impedance match is achieved when the overall net system reactance components are eliminated.

Energy-based medical systems include an energy transmission or signal path that begins at the radiofrequency signal generator, is directed to a patient through an electrode, propagates through the patient to a return electrode, and is returned through a return line to the signal generator. As with any transmission line, impedances along the energy transmission path must be matched to ensure efficient transmission of radiofrequency energy and to minimize reflected power arising from net impedance reactive components. If the impedances along the energy transmission path are not balanced, energy may be reflected within the energy transmission path, making the power and energy delivery inefficient. The reflected energy may inhibit the functionality of the system and consume excess energy. An impedance imbalance or mismatch may occur, for example, if the system component impedance fails to match (and counterbalance) the patient impedance.

Radiofrequency signal generators in conventional energy-based medical systems may include an additional impedance element adapted to match the system component impedance to the patient impedance. For example, signal generators may detect the system impedance and then select an additional conjugate impedance based upon the detected impedance so that overall system reactance is minimized. The impedance element may be, for example, a helical impedance tuning coil (e.g., inductor), or other similar device, positioned internally or proximate to the signal generator to balance a detected system capacitance.

Many energy-based medical systems utilize removable and replaceable electrode assemblies with working electrodes of different sizes and constructions and, hence, different impedances. The electrode assembly and electrode may be changed to adjust the treatment to different patients, to change the type of treatment, or to perform treatments of different types on the same patient. If so equipped, the signal generators in conventional medical systems must detect the change in impedance from the electrode swap and then select a new additional conjugate impedance. As mentioned above, the adjustment of the system impedance maintains an impedance balance that minimizes wasted energy. However, the dynamic range of the selectable additional impedance may be inadequate to handle a full range of working electrodes. In addition, the response time for adjusting the system impedance may be slow.

What is needed, therefore, are energy-based system electrode assemblies and handpieces that can efficiently and rapidly balance the overall system impedance.

SUMMARY OF THE INVENTION

Embodiments of the invention provide energy-based electrode assemblies and handpieces for energy-based medical systems that include impedance assemblies and/or element(s) to facilitate ranged and accurate impedance matching or near-matching, even during changeovers between differently sized electrodes. The electrode assemblies and handpieces, which may be used for cosmetic or therapeutic treatment, are operable to include and/or select an electrical impedance to promote efficient operation of the system.

In an embodiment of the invention, an apparatus includes a handpiece, an electrode assembly removably coupled with the handpiece, an electrical circuit partially in said handpiece and partially in said electrode assembly, and at least one circuit element in at least one of the handpiece or the electrode assembly. The electrode assembly includes an electrode having a dielectric portion and a conductive portion disposed on the dielectric portion. The dielectric portion is adapted to be arranged between the conductive portion and the tissue such that treatment energy is transmitted from the conductive portion through the dielectric portion for capacitively coupling with tissue to perform a non-invasive tissue treatment. The electrical circuit is adapted to electrically couple the conductive portion of the electrode with an energy-generating device. At least one circuit element is configured to introduce at least one impedance into the electrical circuit when the electrode assembly is coupled with the handpiece.

In an embodiment of the invention, an apparatus comprises an electrode assembly adapted to be removably coupled with the handpiece, an electrical circuit at least partially in the electrode assembly, and at least one circuit element in the electrode assembly. The electrode assembly includes an electrode having a dielectric portion and a conductive portion disposed on the dielectric portion. The dielectric portion is adapted to be arranged between the conductive portion and the tissue such that treatment energy is transmitted from the conductive portion through the dielectric portion for capacitively coupling with tissue to perform a non-invasive tissue treatment. The electrical circuit is adapted to electrically couple the conductive portion of the electrode with an energy-generating device. At least one circuit element is configured to introduce at least one impedance into the electrical circuit when the electrode assembly is coupled with the handpiece.

In an embodiment of the invention, an electrode assembly is provided that is adapted for coupling with an energy-generating device to create a tissue-treating system. The electrode assembly comprises an electrode including electrode conducting material and tissue-engaging dielectric material. The electrode is operable to capacitively couple electromagnetic energy from the energy-generating device through the conducting and dielectric materials into and through tissue. An electrode housing supports the electrode with the latter being operably coupled with the energy-generating device. Structure is also located within the housing that causes a desired impedance to be introduced into the system to facilitate at least approximate impedance matching.

In an embodiment of the invention, an apparatus is provided for use with an energy-generating device and an electrode assembly to treat tissue in which the electrode assembly includes an electrode adapted to capacitively couple treatment energy with the tissue to perform a non-invasive tissue treatment. The apparatus comprises a handpiece adapted to removably receive the electrode assembly, an electrical circuit in the handpiece, and at least one circuit element in the handpiece. The electrical circuit is adapted to electrically couple the electrode with the energy-generating device. At least one circuit element is configured to introduce at least one impedance into the electrical circuit when the electrode assembly is coupled with the handpiece.

In an embodiment of the invention, a method is provided for operating an energy-based medical system to treat tissue. The method comprises coupling an electrode assembly in a handpiece to establish an electrical circuit between an electrode in the electrode assembly and an energy-generating device of the energy-based medical system. The method further comprises selecting an impedance based upon at least one circuit element in at least one of the handpiece or the electrode assembly that balances an impedance of the electrode assembly, introducing the supplemental impedance into the electrical circuit, and transferring energy from the electrode assembly to the tissue.

In another embodiment of the invention, a handpiece is provided for use in an energy-based treatment system including an energy-generating device. The handpiece has a handpiece housing configured to receive any one of a number of different electrode assemblies each having an electrode with a different electrical property. The handpiece also includes a coupling assembly carried by the housing and adapted to cooperate with each of the different electrode assemblies in order to couple each of the electrodes with the device and to at least in part determine a unique supplemental impedance to be provided by the system which corresponds to each different electrode respectively.

The impedance element(s) may be selected from the group consisting of an inductor, a capacitor, a resistor, and combinations thereof. Also, the electrode housing may be provided with an actuating arm that cooperates with the handpiece for at least in part selecting a desired supplemental impedance, e.g., the length of the arm is related to the desired supplemental impedance, and the arm actuates handpiece-mounted impedance components, such as a variable switch. Other alternatives include a plurality of electrical contacts and complementary interconnects operable to selectively interconnect the electrode with at least certain of the contacts to vary the supplemental impedance. If desired, a digital memory device may be provided in the electrode assembly or handpiece that stores information utilized by the system to determine the desired supplemental impedance.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION

Figure 1A:
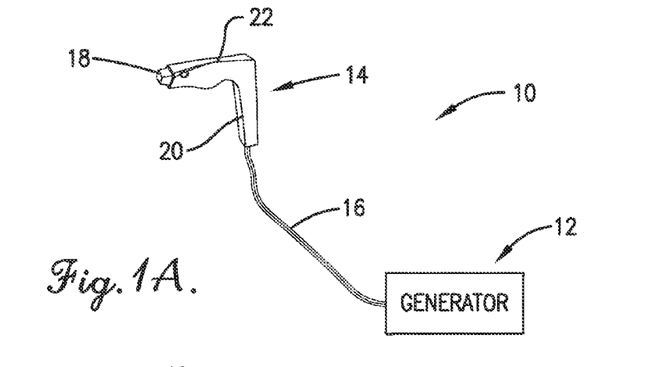
FIG. 1A is a diagrammatic view of an energy-based medical system in accordance with an embodiment of the invention.
Figure 1B:
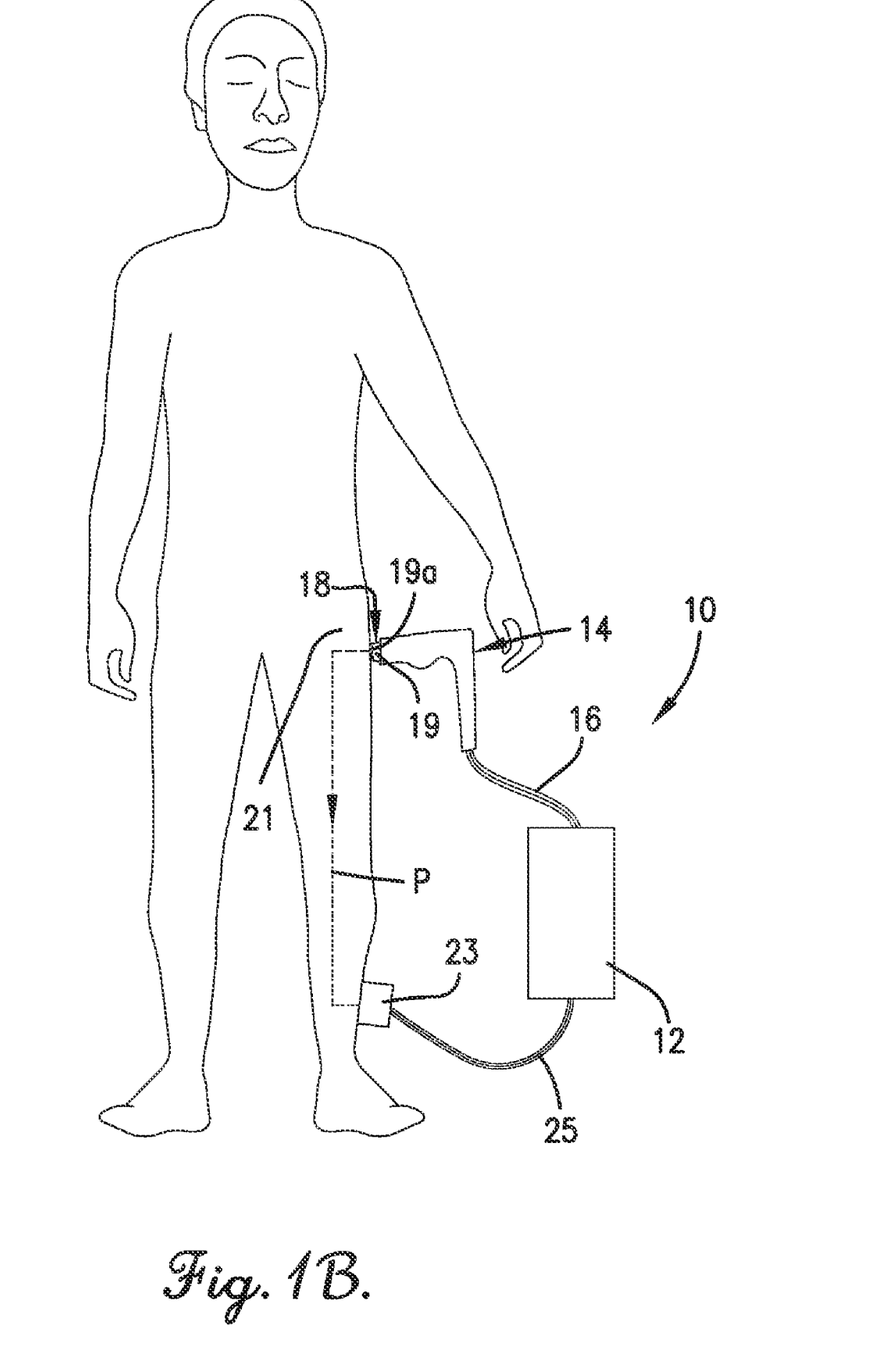
FIG. 1B is a diagrammatic view of the system of FIG. 1A depicted in use during a medical procedure.
Figure 1C:
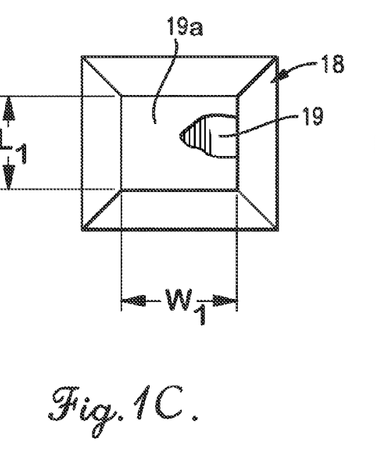
FIG. 1C is a diagrammatic end view of an electrode assembly of the energy-based medical system of FIGS. 1A and 1B wherein part of a conductive layer is shown that lies beneath a dielectric layer.

With reference to FIGS. 1A-C, an energy-based medical system 10 generally includes an energy-generating device or generator 12 and a pistol-type handpiece 14 coupled with generator 12 via a cable 16. The generator 12 may be selected from a variety of generator types, including electromagnetic, radiofrequency, microwave, infrared, optical, laser, acoustic, or ultrasound. Accordingly, a selected generator 12 may generate any corresponding energy magnitude sufficient for purposes of the system 10. System 10 may be used for a variety of therapeutic, medical, and/or cosmetic treatments of a patient.

In one specific embodiment of the invention, the generator 12 may be a radiofrequency (RF) generator that utilizes a capacitive electrode 19 so that the system 10 is RF-based. Such energy-based systems 10 are commercially available from Thermage Inc. (Hayward, Calif.) under the trademark ThermaCool®. Such energy-based systems are also disclosed in U.S. Pat. No. 6,413,255 and U.S. patent application Ser. No. 10/828,703 (U.S. Publication Number 2004/0210214), filed Apr. 21, 2004; the disclosure of each of these patent documents is incorporated herein by reference in its entirety. The RF generator 12 may rely on a crystal oscillator and/or other electronic components to generate an output signal. The output signal of the RF generator 12 may be any impulse or generally fluctuating electric quantity, such as voltage, current, electric field strength, or the like. The output signal may be a generally sinusoidal energy wave having varying current and/or voltage amplitudes. The RF generator 12 may be operable to generate an RF signal in the range of approximately 5 MHz to approximately 7 MHz.

The handpiece 14 includes a grip 20 and forwardly extending barrel 22 presenting a forward socket 24, or other appropriate structure, adapted to receive an electrode assembly 18 forming a working end of the handpiece 14. The electrode assembly 18 includes a conductive electrode 19 and a dielectric layer 19a separating the conductive electrode 19 from the treated tissue so as to capacitively couple RF energy into tissue 21. During use, the dielectric layer 19a is disposed between the conductive electrode 19 and the tissue 21, so that the conductive electrode 19, layer 19a, and tissue 21 are arranged to form an electrical capacitor and create an impedance which is capacitive. The electrode assembly 18 may also include supplemental tunable or selectable impedance assemblies and/or element(s) within the housing thereof, as described herein.

The handpiece 14 and electrode assembly 18 comprise an assembly that may be coupled with the generator 12 through the cable 16. Specifically, the handpiece 14 and electrode assembly 18 are operatively coupled by the cable 16 with generator 12 so that energy is supplied to the handpiece 14 and applied to the patient through electrode 19. The electrical circuit including the handpiece 14 and electrode assembly 18 is completed by the energy passing along a signal or current path, P, and exiting the body at a non-therapeutic return electrode 23 for return to the generator 12 via a return cable 25. The return cable 25 may comprise a part of the cable 16. The return electrode 23 is attached to a body surface of the patient, such as the patient's leg or back. Typically, the electrode assembly 18 is electrically coupled with a terminal of one voltage polarity on the generator 12 and the return electrode 23 is electrically coupled with another terminal of the opposite polarity on the generator 12. The return electrode 23 is non-therapeutic in that no significant heating is produced at its attachment site to the patient's body because a low current density is delivered across a relatively large surface area.

As described herein, the electrode assembly 18 and handpiece 14 may cooperate to promote impedance matching between a patient and the system 10. To that end, the assembly of the electrode assembly 18 and handpiece 14 is provided with an appropriate impedance determining or selecting structure to facilitate a matching impedance or a near-matching impedance between the components of system 10 and the patient. The impedance matching is achieved regardless of the size or impedance of the particular electrode 19 utilized in the system 10. Structure may be included in the system 10 that creates a desired supplemental impedance so that the impedance, as seen by the generator 12, is equal to a value or close to (i.e., approximately equal to) an expected value. As a result, the requirements for fine tuning the impedance at the generator 12 are relaxed. The impedance matching minimizes the reactive component of the overall impedance of the circuit.

Figure 1D:
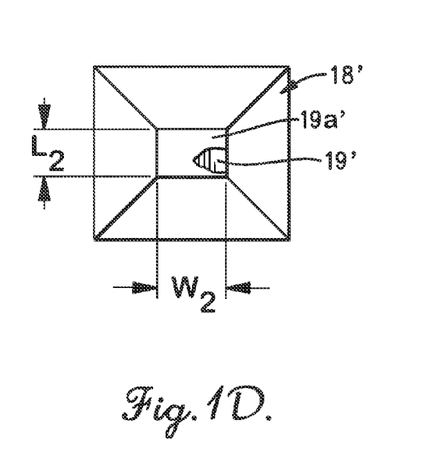
FIG. 1D is a diagrammatic end view similar to FIG. 1C of an electrode assembly also adapted for use with the energy-based medical system of FIGS. 1A and 1B.

With reference to FIG. 1D, an electrode 19' of different surface area, but otherwise identical to electrode 19, may have a significantly different reactive impedance than electrode 19. Electrode 19 has a surface area determined by the product of the length, $l_1$, and width, $w_1$, and electrode 19' has a surface area determined by the product of the length, $l_2$, and width, $w_2$. Electrode 19 has a larger surface area than electrode 19'. Energy is capacitively coupled with the tissue 21 across the surface areas of the electrodes 19, 19' when coupled with the handpiece 14 and operating as a component of system 10 to treat tissue.

In some patient treatments, multiple electrodes 19, 19' of different surface areas may be used to treat a single patient, which requires that the handpiece 14 accept two different electrode assemblies 18, 18' carrying electrodes 19, 19', respectively. The different electrodes 19, 19' may also be used to treat different patients. Changing the surface area of the electrode 19 changes the reactive impedance of the electrodes 19, 19', as understood by a person having ordinary skill in the art, because of the different energy concentrations in large and small electrodes.

The capacitance of the electrodes 19, 19' also generally varies in proportion to the specific electrode surface area. As a specific example, the generator 12 may be pre-tuned to create a conjugate impedance with electrode 19 that presents a nominal 120 pF capacitance. The pre-tuning minimizes the overall circuit reactance. If the electrode assembly 18' carrying electrode 19' has a nominal capacitance different from 120 pF and is coupled with the handpiece 14, an additional impedance may be added such that the electrode assembly 18' presents the 120 pF capacitance regardless of the size or shape of the utilized electrode 19'. In this manner, the impedance tuning circuit of the generator 12 is not required to have an unduly large dynamic range and fine tune system impedance quickly.

As another specific example, electrode 19 may have a 120 pF nominal capacitance and a capacitive reactance of negative 220 ohms at a frequency of 6 MHz. Electrode 19' may have a 30 pF nominal capacitance and a capacitive reactance of negative 880 ohms at 6 MHz. In order to make the electrodes 19, 19' appear to be electrically equivalent, an impedance generally equal to the conjugate reactance of the difference between the two electrodes 19, 19' may be utilized, so that the net reactance presented to the generator 12 remains substantially unchanged regardless of which of the electrodes 19, 19' is coupled with the generator 12. As a specific example, an inductor having an inductance of approximately 17.6 μH and an inductive reactance of positive 660 ohms may be coupled with electrode 19 to enable electrode 19' to have the same effective impedance to the system 10 as electrode 19. As a second example electrode 19' may have a 240 pf nominal capacitance and a capacitive reactance of negative 110 ohms. In this case a capacitor also equal to 240 pf with a capacitive reactance of negative 110 ohms is added to create a combined impedance that is identical to the 120 pf electrode 19 with capacitive reactance of negative 220 ohms. As those skilled in the art will appreciate, innumerable other combinations of electrodes 19, 19' and impedances may be utilized to present any desired total impedance to the generator 12 to minimize any retuning by the generator 12 whenever different electrodes 19, 19' are utilized.

Figure 2:
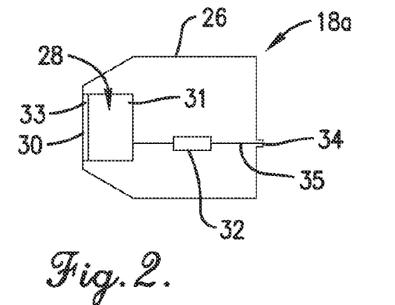
FIG. 2 is a diagrammatic view of an electrode assembly in accordance with an embodiment of the invention.

With reference to FIG. 2 and in one embodiment of the invention, an electrode assembly 18a includes an electrode 28 with a working face 30, an outermost housing 26 supporting the electrode 28, and an impedance assembly 32. The impedance assembly 32 is electrically coupled with the electrode 28 and is also electrically coupled to a coupling contact 34 located rearward of electrode 28 by one or more leads 35. The electrode assembly 18a is designed for receipt within a socket of handpiece 14 (FIG. 1A) that includes a contact (not shown) mating with contact 34 to complete an electrical connection from generator 12 to the electrode assembly 18a. In this embodiment, the handpiece 14 lacks any supplemental impedance components, as described herein.

Electrode 28 includes a conductor layer 31, typically a metal, and a dielectric layer 33 that presents the working face 30 contacting the tissue 21 during use. The dielectric layer 33 is arranged or disposed between the conductor layer 31 and the tissue 21 such that, during a non-invasive tissue treatment, the energy is transmitted from the conductor layer 31 through the dielectric layer 33 by capacitively coupling with the tissue 21.

The electrical coupling of the electrode assembly 18a to the generator 12 enables the impedance assembly 32 to provide an impedance upon energization of the electrode assembly 18a by the generator 12. The impedance of the impedance assembly 32 is at least generally related to the impedance of the electrode 28 to facilitate operation of the system 10, as described above. Thus, the combination of the electrode 28 and the impedance assembly 32 provides a total impedance for the handpiece/electrode assembly corresponding to a desired impedance range related to the impedance of the electrode 28. Lead 35 electrically couples the electrode 28 and the impedance assembly 32 in an electrical circuit with the generator 12.

It will be understood that the impedance assembly 32 may include one or more circuit elements, such as inductors, capacitors, resistors, and any combination thereof. For example, the impedance assembly 32 may include two or more inductors and capacitors arranged in a parallel, serial, or other similar configurations. Similarly, the electrode assembly 18a may include one or more additional elements (not shown), such as a switch, to enable the system 10 or a user to select one or more of the inductors, capacitors, and/or resistors that comprise the impedance assembly 32 included within the electrode assembly 18a. The impedance assembly 32 may comprise a variable capacitor device (i.e., varactor) or a variable inductor device.

In one embodiment of the invention, the impedance assembly 32 comprises a single inductor or single capacitor to limit the complexity of the electrode assembly 18a. In a particular embodiment, the single inductor may be a toroidal inductor, which provides low stray RF leakage, a high Q (i.e., quality-factor), and simplified physical implementation.

Figure 3:
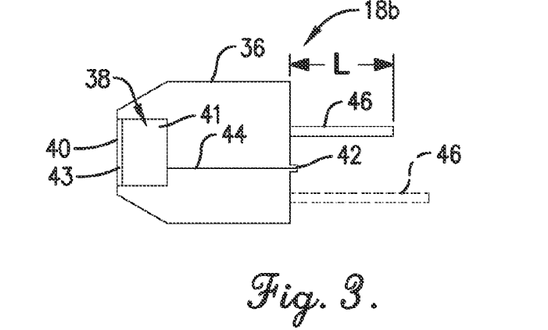
FIG. 3 is a diagrammatic view of an electrode assembly in accordance with an embodiment of the invention in which the electrode assembly includes an actuating arm.
Figure 4:
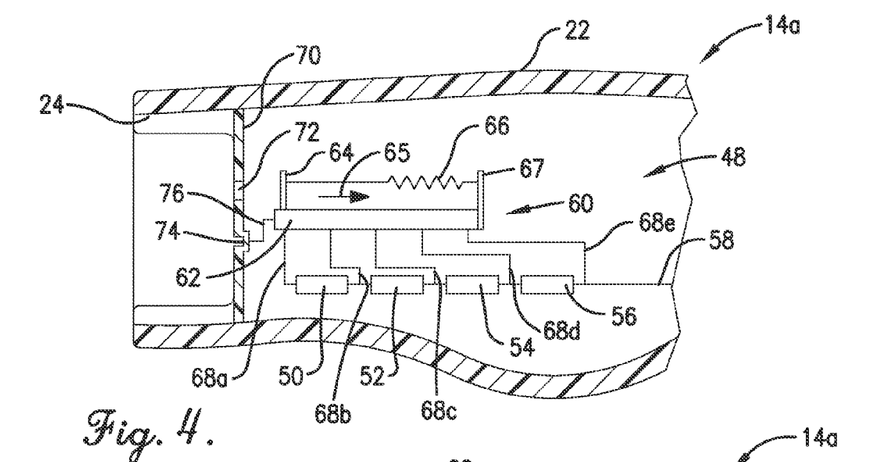
FIG. 4 is a fragmentary diagrammatic view in partial cross-section of a handpiece in accordance with an embodiment of the invention that is adapted to receive the electrode assembly of FIG. 3.
Figure 5:
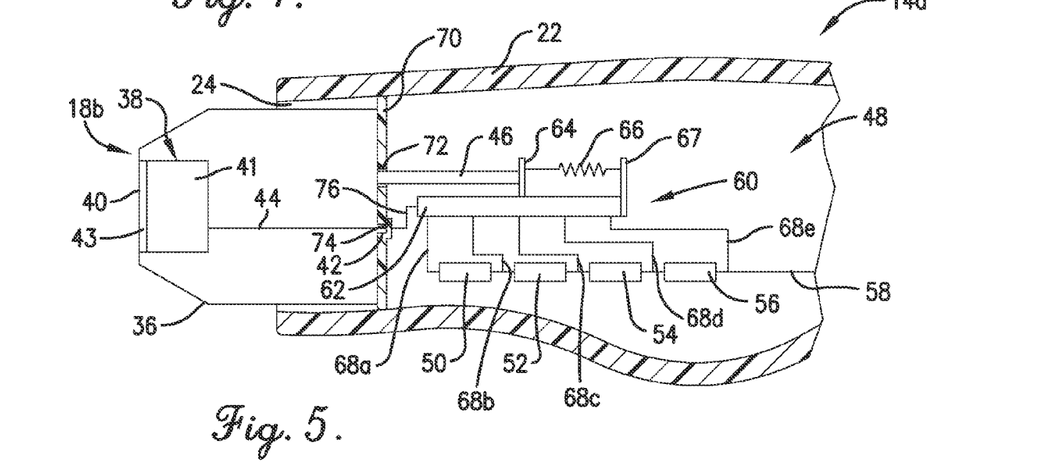
FIG. 5 is a fragmentary diagrammatic view in partial cross-section of a unit formed by operatively coupling the electrode assembly of FIG. 3 with the handpiece of FIG. 4.

With reference to FIGS. 3-5 and in accordance with an alternative embodiment of the invention, an electrode assembly 18b, which is similar to electrode assembly 18 (FIGS. 1A, 1B), is combined with a handpiece 14a (FIG. 4), which is similar to handpiece 14 (FIGS. 1A, 1B), to provide the assembled unit of FIG. 5. Electrode assembly 18b includes an electrode 38 having a working face 40 and an outer housing 36 supporting the electrode 38. Housing 36 also includes circuitry with a contact 42 and a lead 44 coupling contact 42 with the electrode 38. Housing 36 includes an actuating assembly in the form of one or more rearward extending contact or actuating arms 46 configured for mating with the handpiece 14a in order to select a desired supplemental impedance.

Electrode 38, which is similar to electrode 28, includes a conductor layer 41, typically a metal, and a dielectric layer 43 that presents the working face 40 contacting the tissue 21 during use. The dielectric layer 43 is arranged between the conductor layer 41 and the tissue 21 such that, during a non-invasive tissue treatment, energy is transmitted from the conductor layer 41 through the dielectric layer 43 by capacitively coupling with the tissue 21.

Referring to FIG. 4, a socket 24 of handpiece 14a includes an inner wall 70 with an aperture 72 and a contact 74. The circuitry of handpiece 14a includes an internal, selective impedance assembly 48 housed within a barrel 22 at a location rearward of the socket 24 such that the inner wall 70 separates the selective impedance assembly 48 from the socket 24. The selective impedance assembly 48 includes a plurality of impedance elements 50, 52, 54, 56 interconnected along a lead 58, as well as a multi-position switch 60. The switch 60 has an elongated slide contact 62, as well as a shiftable contact 64. The shiftable contact 64 is biased to a default position by means of a spring 66 and a support 67. The contact 74 within the socket 24 is electrically coupled with the slide contact 62 by a lead 76. Lead 58, which is inside the handpiece 14a, is electrically coupled with the generator 12 through an electrically isolated conductor in cable 16 (FIGS. 1A, 1B).

Respective leads 68a-68e interconnect portions of the contact 62 and the lead 58 so that different impedance elements 50, 52, 54, 56 or groups of impedance elements 50, 52, 54, 56 are coupled in the electrical circuit with the electrode 38 and the generator 12. Lead 68a intersects the lead 58 such that, if shiftable contact 64 is positioned relative to slide contact 62 to establish an electrical contact with lead 68a, all of the impedance elements 50, 52, 54, 56 are in the electrical circuit. Lead 68b intersects the lead 58 between impedance elements 50 and 52 such that, if shiftable contact 64 is positioned relative to slide contact 62 to establish an electrical contact with lead 68b, impedance elements 52, 54, 56 are in the electrical circuit. Impedance element 50 is omitted from the circuit for this location of shiftable contact 64.

Lead 68c intersects the lead 58 between impedance elements 52 and 54 such that, if shiftable contact 64 is positioned relative to slide contact 62 to establish an electrical contact with lead 68c, impedance elements 54, 56 are in the electrical circuit. Impedance elements 50, 52 are omitted from the circuit for this location of shiftable contact 64. Lead 68d intersects the lead 58 between impedance elements 54 and 56 such that, if shiftable contact 64 is positioned relative to slide contact 62 to establish an electrical contact with lead 68d, impedance element 56 is in the electrical circuit. Impedance element elements 50, 52, 54 are omitted from the circuit for this location of shiftable contact 64. Lead 68e intersects the lead 58 such that, if shiftable contact 64 is positioned relative to slide contact 62 to establish an electrical contact with lead 68e, none of the impedance elements 50, 52, 54, 56 are in the electrical circuit.

The impedance assembly 48 is operable to provide an impedance upon energization of the impedance assembly 48 by the generator 12. Furthermore, the impedance assembly 48 is capable of providing different impedance levels that at least generally relate to the impedance of the electrode 38. Thus, switch 60 permits the impedance assembly 48 to automatically select one of the different impedance levels upon when the electrode assembly 18b is coupled with the handpiece 14a.

For example, the length, L, of actuating arm 46 may be related to the impedance of electrode 38 so that, when electrode assembly 18a is installed in the socket 24 of handpiece 14a, an appropriate impedance is presented by the assembly 48. As best shown in FIG. 5, the rearward end of the housing 36 abuts, or is in close relationship with, wall 70 when the electrode assembly 18a is seated within socket 24. In this state, the arm 46 extends through aperture 72, engages shiftable contact 64, and displaces or moves shiftable contact 64 from a home position against the bias of spring 66 in a direction 65 until the contact 64 achieves a desired rest position along the length of slide contact 62. This rest position of the shiftable contact 64 corresponds with a selected impedance related to the impedance of electrode 38. Further, contact 42 of housing 36 mates with contact 74 provided in wall 70. In one embodiment of the invention, the presented impedance is at least generally related to the impedance of the electrode 40 to facilitate in operation of the system 10 as described above.

The handpiece 14a may accommodate electrode assemblies 18b having different electrodes 38 and/or working faces 40, while providing an appropriate impedance for each such different electrode assembly. To that end, the length of the respective actuating arm 46 on different electrode assemblies 18b may be correlated with the appropriate impedance desired for that specific assembly or electrode, so that the shiftable contact 64 is shifted along slide contact 62 the necessary distance to achieve the needed impedance. Accordingly, a single handpiece 14a may readily accommodate a variety of different electrode assemblies 18b and rely on the impedance assembly 48 automatically adjust the impedance to match the impedance of the selected electrode assembly 18b.

The switch 60 of handpiece 14a may be designed so that the switch default position shown in FIG. 4 corresponds to a state of no added supplemental impedance. In this instance, the leads 68a-e would be reconfigured so that, when the switch 60 is in the switch default position, none of the impedance elements 50, 52, 54, 56 are in the electrical circuit. Therefore, the handpiece 14a may be used with electrode assemblies that lack an actuating arm, such as assembly 18a (FIG. 2). In such cases, the handpiece-mounted impedance assembly 48 remains in the default position and the shiftable contact 64 remains stationary in a home position.

The operational flexibility is obtained without the use of complex system components such as microprocessor controllers or external power sources, thereby permitting more microprocessor resources to be devoted to other system elements. This simplicity of design also renders the handpiece/electrode assembly combination inexpensive and exceptionally reliable in operation.

Similar to the impedance assembly 32 (FIG. 3), a variety of components may be used as the impedance elements 50, 52, 54, 56, and such components may be interconnected in a variety of ways. In one example, each of the elements 50, 52, 54, 56 may be made up of two or more inductors and capacitors arranged in parallel, serial, or other configuration.

Figure 6:
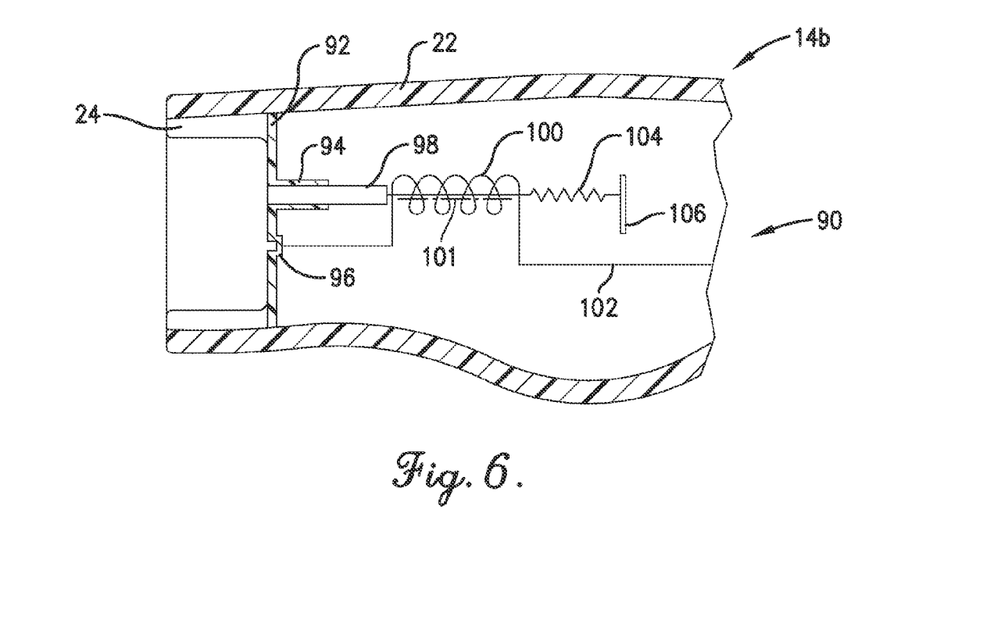
FIG. 6 is a fragmentary diagrammatic view similar to FIG. 4 of a handpiece in accordance with an embodiment of the invention that is equipped with a rod of a magnetically permeable material and a coil wrapped about the rod.
Figure 7:
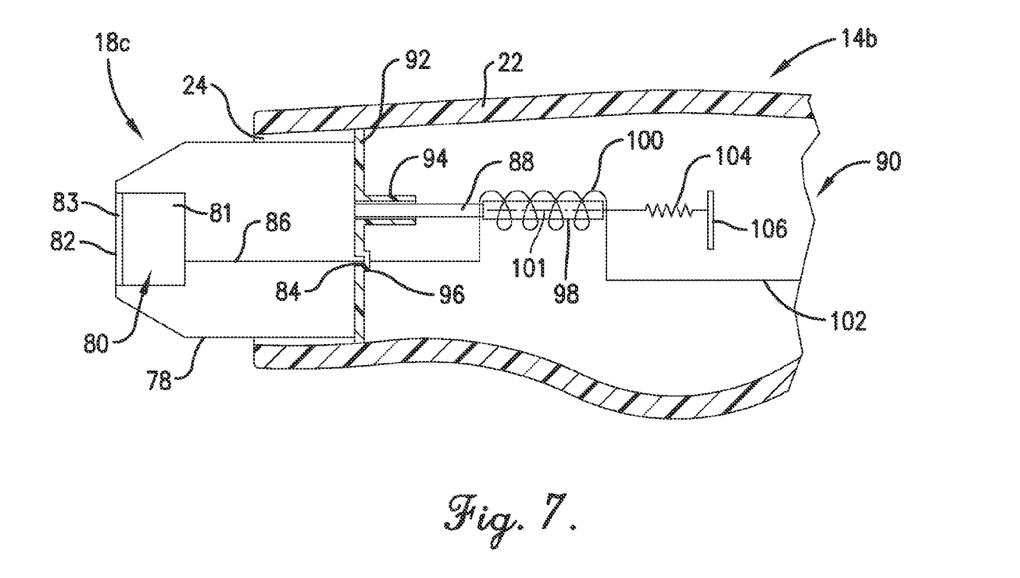
FIG. 7 is a fragmentary diagrammatic view in partial cross-section of a unit formed by operatively coupling the electrode assembly of FIG. 3 with the handpiece of FIG. 6.

With reference to FIGS. 6 and 7 and in accordance with an alternative embodiment of the invention, the electrode assembly 18 (FIGS. 1A, 1B) may comprise an electrode assembly 18c used in conjunction with handpiece 14b to form the combination unit of FIG. 7. The electrode assembly 18c includes an electrode 80 having a working face 82 and a housing 78 supporting the electrode 80. The rear wall of the housing 78 includes a contact 84 connected by one or more leads 86 with electrode 80. An arm 88 comprises an actuating assembly that extends rearward from the housing 78.

Electrode 80 includes a conductor layer 81, typically a metal, and a dielectric layer 83 that presents the working face 82 contacting the tissue 21 during use. The dielectric layer 83 is arranged or disposed between the conductor layer 81 and the tissue 21 such that, during a non-invasive tissue treatment, the energy is transmitted from the conductor layer 81 through the dielectric layer 83 by capacitively coupling with the tissue 21.

The handpiece 14b includes circuitry comprising an internal induction assembly 90 within barrel 22 and rearward of a socket wall 92. The socket wall 92 has a tubular guide sleeve 94 and a contact 96 that mates with housing contact 84. The internal induction assembly 90 includes a core member or rod 98 formed of a permeable magnetic material, such as a low-permeability ferritic stainless steel, and an induction coil 100 that cooperate to provide a variable impedance contingent upon the relative position of the rod 98 relative to the induction coil 100. One end of the induction coil 100 is electrically connected with contact 96 and the opposite end of the induction coil 100 is electrically coupled with generator 12 by a lead 102 and cable 16 (FIGS. 1A, 1B) to define an electrical circuit with the electrode 81.

Windings of the induction coil 100, which comprise a length of an insulated conductor, are wrapped helically about an axis 101. The rod 98 is arranged generally coaxially with the axis 101. Lead 102 is inside the handpiece 14b. Rod 98 is biased to a rest or default position (FIG. 6) by a spring 104 compressed between the rod 98 and a fixed support 106.

When electrode assembly 18c is seated within socket 24 of handpiece 14b, the housing contact 84 mates with handpiece contact 96 to complete an electrical connection between the induction coil 100 and electrode 82. The actuating arm 88 extends through wall 92 and along the length of sleeve 94 so as to shift rod 98 rearward along axis 101 against the bias of spring 104 and into the coil 100 by a distance dictated by the length of actuating arm 88. The extent of shifting of the rod 98 in turn determines the impedance developed in the assembly 90. The impedance of the assembly 90 is a function of the number of coil turns located within coil 100, the magnetic permeability of the magnetically permeable material forming the rod 98, and the current passing through the coil 100.

In the default position of rod 98 shown in FIG. 6, the assembly 90 will generate no supplemental impedance. However, when the rod 98 is shifted along axis 101 partially or wholly within coil 100 owing to the length of actuating arm 88, an impedance is developed based upon the relative position of the rod 98 to that of the coil 100. The length of arm 88 is generally related to the impedance selected for electrode 80. Different electrode assemblies 18c requiring different impedances may be accommodated simply by providing an actuating arm 88 of appropriate length for the selected assembly 18c. The changing supplemental impedance developed by the assembly 90 results from the degree to which rod 98 fills the space radially inside coil 100, as opposed to filling by air having a lower permeability than the rod 98. The location of the rod 98 relative to the coil 100 determines the degree of filling. Thus, a large range of different impedances can be provided by the assembly 90 as each different position of the rod 98 within the coil 100 provides a generally different impedance.

The embodiment of FIGS. 6 and 7 provides operational flexibility without the use of complex system components such as microprocessor controllers or external power sources. This enhances the reliability of the handpiece/electrode assembly combination.

In an alternative embodiment, the arm 88 may be integral with rod 98, such that insertion of the arm 88 into the handpiece 14b positions the integral rod 98 in relation to the coil 100 to provide a supplemental impedance. Such a configuration may be desirable as it reduces the complexity of the handpiece 14b and the need to generally align the arm 88 with the rod 98.

Figure 8:
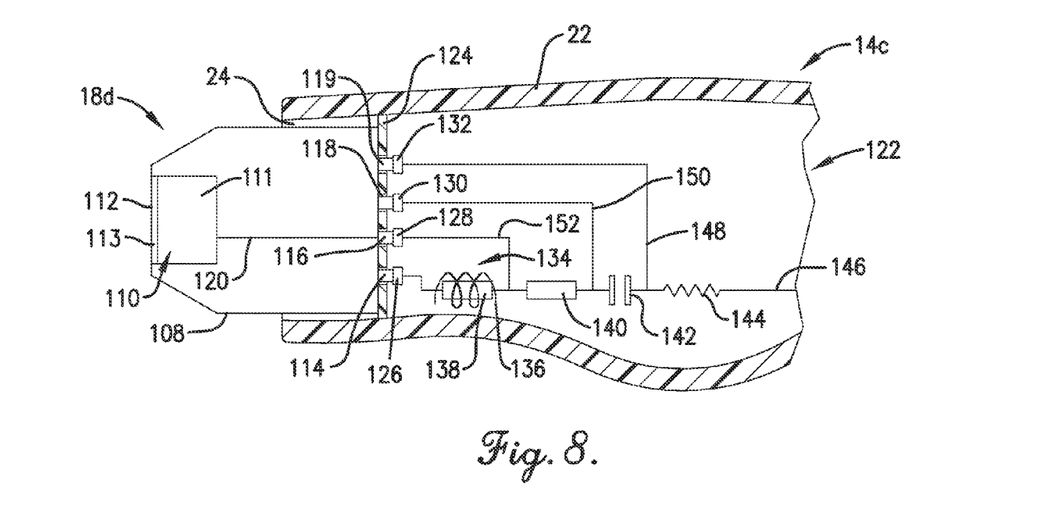
FIG. 8 is a fragmentary diagrammatic view in partial cross-section of a handpiece and an electrode assembly operatively coupled with the handpiece in accordance with an embodiment of the invention in which the handpiece carries multiple contacts and multiple impedance elements and the electrode assembly connects to a subset of the contacts to select specific impedance elements for supplying a desired supplemental impedance.

With reference to FIG. 8 and in accordance with an alternative embodiment of the invention, an electrode assembly 18d is used in combination with a handpiece 14c, as depicted in FIG. 7. The electrode assembly 18d includes an electrode 110 having a working face 112 and a housing 108 supporting electrode 110. Electrode 110 includes a conductor layer 111, typically a metal, and a dielectric layer 113 that presents the working face 112 contacting the tissue 21 during use. The dielectric layer 113 is arranged or disposed between the conductor layer 111 and the tissue 21 such that, during a non-invasive tissue treatment, the energy is transmitted from the conductor layer 111 through the dielectric layer 113 by capacitively coupling with the tissue 21.

A rear surface of the housing 108 includes a plurality of electrical contacts 114, 116, 118, 119. Any one of these electrical contacts 114, 116, 118, 119, according to the specific configuration of electrode assembly 18d, may be electrically connected through a lead 120 to electrode 110 to provide different supplemental impedances. For example, the electrode assembly 18d is shown representatively with lead 120 connected to contact 116. Alternatively, lead 120 may be electrically coupled with any of the other electrical contacts 114, 118, 119.

Handpiece 14c includes an internal impedance assembly 122 and a socket wall 124 having plural spaced-apart electrical contacts 126, 128, 130, 132. The impedance assembly 122 includes an inductor 134 including a coil 136 and a rod 138, an impedance element 140, a capacitor 142, and a resistor 144. These components are wired in series through a lead 146, which terminates at contact 126, and are coupled with the generator 12. Lead 146, which is inside the handpiece 14a, is electrically coupled with the generator 12 through cable 16 (FIGS. 1A, 1B).

In operation, the electrode assembly 18d is at least partially received by the handpiece 14c such that the electrical contacts 114, 116, 118, 119 mate with the electrical contacts 126, 128, 130, 132 to electrically couple the electrode assembly 18d to the handpiece 14c. However, only one of the electrical contacts 114, 116, 118, 119 is electrically coupled by lead 120 with the conductor layer 111 of the electrode 110. Upon energization of the system 10, lead 120 provides a current path through one or more of the impedance elements 134, 140, 142, and 144 to provide a desired supplemental impedance in the electrical circuit between the generator 12 and electrode 110. If lead 120 is coupled with a different one of the electrical contacts 114, 118, 19, then the mating of electrical contacts 114, 116, 118, 119 with the electrical contacts 126, 128, 130, 132 will close a different electrical circuit that includes a different set of the impedance elements 134, 140, 142, and 144 to provide different levels of impedance. As described above, the provided impedance may at least generally relate to the impedance of the electrode 110.

In the representative embodiment in which lead 120 is coupled with contact 116, the impedance assembly 122 employs three of the four impedance elements 134, 140, 142, and 144 to develop the desired supplemental impedance. As is readily apparent to a person having ordinary skill in the art, the impedance elements 134, 140, 142, and 144 may be wired in various configurations so that some would be in series, some in parallel, and some excluded from the assembly 122 altogether. Similarly, additional contacts and/or impedance elements (not shown) may be utilized to further increase the number of available impedance levels. In this way, a large number of different impedance values can be provided.

Figure 9:
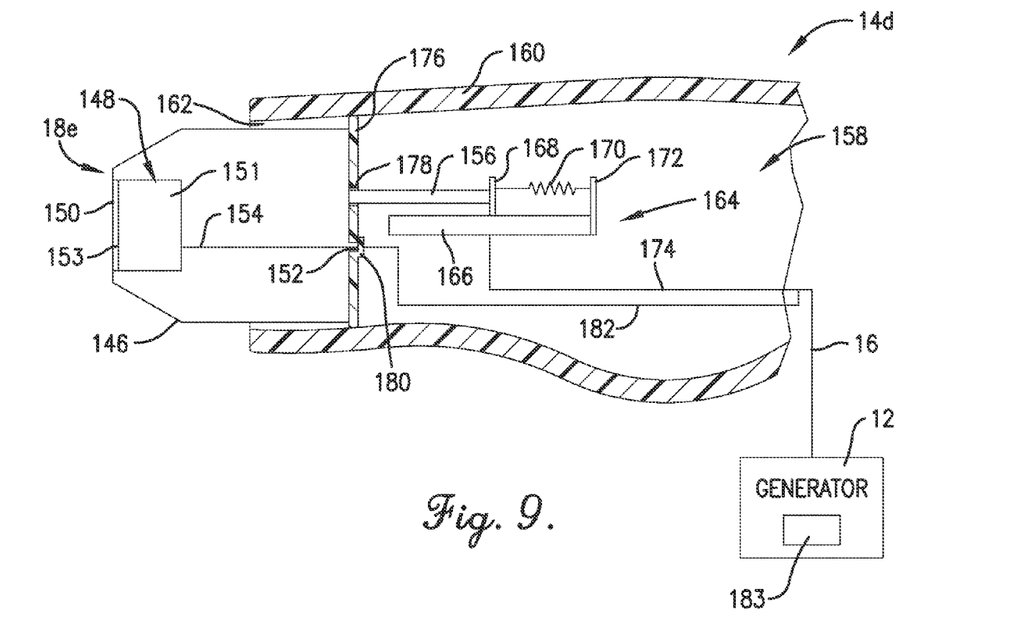
FIG. 9 is a fragmentary diagrammatic view in partial cross-section of a handpiece and an electrode assembly operatively coupled with the handpiece in accordance with an embodiment of the invention in which the handpiece has an impedance selection assembly actuated by an electrode assembly, the impedance selection assembly is coupled with a system generator, and the selection assembly in the handpiece determines the supplemental impedance supplied by one or more impedance elements associated with the generator.

With reference to FIG. 9 and in accordance with an alternative embodiment of the invention, an electrode assembly 18e is combined together with a handpiece 14d to provide a combined unit. The electrode assembly 18e includes an electrode 148 having a working face 150 and an outer housing 146 supporting the electrode 148. Electrode 148 includes a conductor layer 151, typically a metal, and a dielectric layer 153 that presents the working face 150 contacting the tissue 21 during use. The dielectric layer 153 is arranged or disposed between the conductor layer 151 and the tissue 21 such that, during a non-invasive tissue treatment, the energy is transmitted from the conductor layer 151 through the dielectric layer 153 by capacitively coupling with the tissue 21.

The housing 146 of the electrode assembly 18e also includes circuitry with a contact 152 electrically coupled by a lead 154 to the electrode 148 and an actuating assembly in the form of one or more rearward extending contacts or actuating arms 156 configured for mating with the handpiece 14d in order to select a supplemental impedance. The handpiece 14d includes an internal impedance selection assembly 158 housed within a barrel 160 rearward of a socket 162. The impedance selection assembly 158 in this embodiment includes a multi-position switch 164. The switch 164 has an elongated slide contact 166 as well as a shiftable contact 168, the latter biased to a default position by means of a spring 170 and a support 172. One or more leads 174, which are inside the handpiece 14d, electrically couple the switch 164 to the generator 12 via cable 16.

The socket 162 of handpiece 14d includes an inner wall 176 with a through-opening 178 and a contact 180. The contact 180 is electrically coupled to the generator through a lead 182. Leads 174 and 182 in handpiece 14d are connected with electrically isolated conductors in the cable 16.

The impedance selection assembly 158 is operatively coupled with the generator 12 to provide a supplemental impedance upon energization of the generator 12. The assembly 158 is capable of providing different supplemental impedances that may at least generally relate to the impedance of the corresponding electrode 148. Specifically, the assembly 158 is operable to provide a signal to the generator 12 through the lead 174 that corresponds to the position of the switch 164 and, thus, the impedance of the electrode 148. This enables the generator 12 to select one or more impedances utilizing impedance elements 183, such as a controlled tuning coil or a network of impedance elements, that are associated with the generator 12 and place the selected impedance in the electrical circuit coupling the generator 12 with the electrode 186.

The length of actuating arm 156 is related to the impedance of electrode 148 so that, upon installation of the electrode assembly 18e within the socket 162 of handpiece 14d, the arm 156 engages the switch 164. When the electrode assembly 18e is fully seated within socket 162, the rearward end of the housing 146 abuts or is in close relationship with wall 176. In this orientation, the arm 156 extends through opening 178 and engages shiftable contact 168 and moves the same against the bias of spring 170 until the contact 168 achieves a desired rest position along the length of slide contact 166. This rest position corresponds with the desired supplemental impedance that is based on the impedance of electrode 148. As such, the impedance selection assembly 158 provides a signal corresponding to the rest position of switch 164, the latter determined by the length of arm 156.

The generator 12 receives the signal from the impedance selection assembly 158, which comprises an analog switching device, and uses this signal to determine an appropriate supplemental impedance for utilization with the selected electrode 148. For example, the generator 12 may include circuitry or an embedded computer program for selecting an impedance utilizing the impedance element(s) 183, based upon the provided signal. Such circuitry or program may include a look-up table to quickly enable the system 10 to determine a desired impedance based upon the output signal from assembly 158. The selected supplemental impedance in coupled with the electrical circuit connecting the generator 12 with the electrode 151.

It will be appreciated that different electrode assemblies will present different impedances, and will thus be provided with switch-actuating arms of different lengths corresponding or related to the appropriate system impedance to be developed via element(s) 183 in generator 12.

Figure 10:
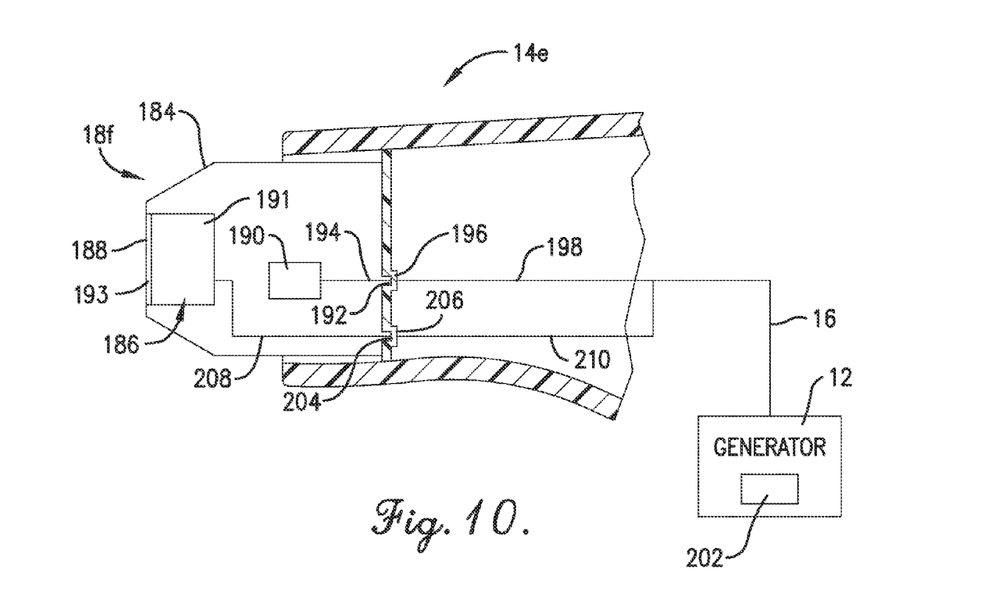
FIG. 10 is a fragmentary diagrammatic view in partial cross-section of a handpiece and an electrode assembly operatively coupled with the handpiece in accordance with an embodiment of the invention in which the electrode assembly carries a memory storing impedance selection information for selecting a supplemental impedance to be supplied by one or more impedance elements associated with the generator.

With reference to FIG. 10 and in accordance with an alternative embodiment of the invention, an electrode assembly 18f is placed in a mating relationship with handpiece 14e to form a combined unit. The electrode assembly 18f includes an electrode 186 presenting a working face 188, an outermost housing 184 supporting the electrode 186, and a memory 190. Electrode 186 includes a conductor layer 191, typically a metal, and a dielectric layer 193 that presents the working face 188 in contact with the tissue 21 during use. The dielectric layer 193 is arranged or disposed between the conductor layer 191 and the tissue 21 such that, during a non-invasive tissue treatment, the energy is transmitted from the conductor layer 191 through the dielectric layer 193 by capacitively coupling with the tissue 21.

The electrode assembly 18f includes a coupling contact 204 for coupling the assembly 18f with a corresponding contact 206 of the handpiece 14e. One or more leads 208 electrically connect the electrode 186 to the contact 192. Handpiece 14e has one or more leads 210 to complete an electrical circuit extending from the electrode 186 to generator 12.

The electrode assembly 18f has another coupling contact 192 for coupling the assembly 18f with a corresponding contact 196 of the handpiece 14e. One or more leads 194 electrically connect the memory 190 to the contact 192. Handpiece 14e has one or more leads 198 to complete an electrical connection from the memory 190 to generator 12. Leads 198 and 210 in handpiece 14e are connected with electrically isolated conductors in the cable 16.

The memory 190 stores information or data that is generally related to the impedance of the electrode 186. The memory 190 may be an erasable programmable read-only memory (EPROM) operable to be programmed to include data corresponding to the impedance of the electrode 186. The data stored within the memory 190 may include data indicating the size, shape, nominal capacitance, and impedance of the electrode 186. Additionally, the memory 190 may include data corresponding to existence of an integral impedance assembly, such as the assembly described in the embodiment of FIG. 2.

The generator 12 reads information stored by the memory 190 in a conventional manner by sending or receiving signals through the lead 198, which is inside the handpiece 14e, and the corresponding conductor(s) in cable 16. The generator 12 includes circuitry and an impedance-selecting element 202, such as a tuning coil or network of impedance elements. The circuitry includes logic, such as hardware or an embedded computer program, to determine a desired impedance in response to a data signal from memory 190. For example, the generator 12 may read the memory 190 to determine the impedance of the electrode 186, utilize a look-up table to determine a desired impedance, and control the impedance selecting element 202 to provide the desired impedance.

Thus, the memory 190 enables the generator 12 to quickly determine the electrical characteristics of the electrode 186 to expedite impedance matching without the need to utilize current or voltage sensors to detect the impedance of the electrode 186.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. For example, the impedance assemblies disclosed herein may be positioned within the handpiece 14, electrode assembly 18, or both, individually or simultaneously. Similarly, various other combinations, such as combining the impedance assembly 32 with one or more of the actuating arms 46 and handpiece impedance assembly 48, utilizing actuating arms 46 that have a configuration that corresponds to width, shape, or other sizes instead of or in addition to length, etc, may be utilized to produce various desired effects. Accordingly, departures may be made from such details without departing from the spirit or scope of applicants' general inventive concept.

What is claimed is:

1. An apparatus for use with an energy-generating device to treat tissue of a patient, said apparatus comprising:
    a handpiece;
    an electrode assembly removably coupled with said handpiece, said electrode assembly including an electrode having a dielectric portion and a conductive portion disposed on said dielectric portion, and said dielectric portion adapted to be arranged between said conductive portion and the tissue such that treatment energy is transmitted from said conductive portion through said dielectric portion for capacitively coupling with the tissue to perform a non-invasive tissue treatment;
    an electrical circuit partially in said handpiece and partially in said electrode assembly, said electrical circuit adapted to electrically couple said conductive portion of said electrode with the energy-generating device; and
    at least one circuit element in at least one of said handpiece or said electrode assembly, said at least one circuit element configured to introduce at least one impedance into said electrical circuit when said electrode assembly is coupled with said handpiece, said at least one impedance being sized to reduce an impedance difference between a patient and a combination of the apparatus and the energy-generating device.

2. The apparatus of claim 1 wherein said at least one circuit element comprises at least one impedance element in said handpiece, said at least one impedance element selected from the group consisting of an inductor, a capacitor, a resistor, and combinations thereof.

3. The apparatus of claim 1 wherein said at least one circuit element further comprises a variable inductor device in said electrical circuit in said handpiece, and said electrode assembly is configured to cooperate with said variable inductor device for changing an inductance of said variable inductor device to introduce said at least one impedance into said circuit.

4. The apparatus of claim 3 wherein said electrode assembly includes a housing and an actuating arm projecting from said housing, and said variable inductor device includes a first member and a second member movable relative to said first member in response to a stimulus from said actuating arm for changing said inductance of said variable inductor device.

5. The apparatus of claim 4 wherein said first member comprises a coil having a helical arrangement about an axis, and said second member comprises a core member formed from a magnetically permeable material, said core member movable along said axis between at least first and second positions relative to said coil to introduce different inductances into said electrical circuit.

6. The apparatus of claim 5 wherein said actuating arm and said core member are positioned to physically contact to supply said stimulus, and said actuating arm has a length sufficient to move said core member to at least one of said first and second positions.

7. The apparatus of claim 1 wherein said at least one circuit element comprises first and second impedance elements in said handpiece and a switch in said handpiece, said first and second impedance elements having different impedances, and said switch configured to be switched to introduce at least one of said first and second impedance elements into said electrical circuit.

8. The apparatus of claim 7 wherein said switch includes a first contact and a second contact movable relative to said first contact between a first position in which said first and second impedance elements are in said electrical circuit and a second position in which said second impedance element is in said electrical circuit.

9. The apparatus of claim 8 wherein said electrode assembly includes a housing and an actuating arm projecting from said housing, and said first contact is movable between said first and second positions in response to a stimulus from said actuating arm.

10. The apparatus of claim 9 wherein said actuating arm and said first contact physically contact to supply a movement force comprising said stimulus, and said actuating arm has a length sufficient to move said first contact to at least one of said first and second positions.

11. The apparatus of claim 1 wherein said at least one circuit element is in said electrode assembly.

12. The apparatus of claim 1 wherein said at least one circuit element further comprises first and second impedance elements in said handpiece and first and second electrical contacts in said handpiece, said first and second impedance elements having different impedances, and said first electrical contact electrically coupling said first and second impedance elements in said electrical circuit and said second electrical contact electrically coupling said second impedance element in said electrical circuit.

13. The apparatus of claim 12 wherein said electrode assembly comprises an electrical contact electrically coupled with said conductive portion, said electrical contact of said electrode assembly electrically coupled with one of said first and second electrical contacts.

14. The apparatus of claim 1 wherein said at least one circuit element comprises a digital memory device storing data relating to said at least one impedance, said digital memory device adapted to transfer said data to the energy-generating device so that the energy-generating device can introduce said at least one impedance to said electrical circuit.

15. The apparatus of claim 14 wherein said digital memory device is located in said electrode assembly.

16. The apparatus of claim 1 wherein said electrical circuit includes a switch in said handpiece, said switch configured to be switched between first and second positions correlated with different impedances, and said switch adapted to indicate to the energy-generating device which of said first and second positions is selected such that the energy-generating device can supply a respective one of the different impedances to said electrical circuit.

17. The apparatus of claim 16 wherein said switch includes a first electrical contact and a second electrical contact movable relative to said first electrical contact to provide said first and second positions.

18. The apparatus of claim 17 wherein said electrode assembly includes a housing and an actuating arm projecting from said housing, and said first electrical contact is movable between said first and second positions in response to a stimulus from said actuating arm.

19. The apparatus of claim 18 wherein said actuating arm and said first electrical contact physically contact to supply a movement force comprising said stimulus, and said actuating arm has a length sufficient to move said first contact to at least one of said first and second positions.

20. An apparatus for use with a handpiece of an energy-generating device to treat tissue of a patient, said apparatus comprising:
   an electrode assembly adapted to be removably coupled with the handpiece, said electrode assembly including an electrode having a dielectric portion and a conductive portion disposed on said dielectric portion, and said dielectric portion adapted to be arranged between said conductive portion and the tissue such that treatment energy is transmitted from said conductive portion through said dielectric portion for capacitively coupling with the tissue to perform a non-invasive tissue treatment;
   an electrical circuit at least partially in said electrode assembly, said electrical circuit adapted to electrically couple said conductive portion of said electrode with the energy-generating device; and
   at least one circuit element in said electrode assembly, said at least one circuit element configured to introduce at least one impedance into said electrical circuit when said electrode assembly is coupled with the handpiece, said at least one impedance being sized to reduce an impedance difference between a patient and a combination of the apparatus and the energy-generating device.

21. The apparatus of claim 20 wherein said at least one circuit element comprises a digital memory device storing data relating to said at least one second impedance, said digital memory device adapted to transfer said data to the energy-generating device so that the energy-generating device can supply said at least one impedance to said electrical circuit.

22. The apparatus of claim 20 wherein said at least one circuit element comprises at least one impedance element, said at least one impedance element selected from the group consisting of an inductor, a capacitor, a resistor, and combinations thereof.

23. An apparatus for use with an energy-generating device and an electrode assembly to treat tissue of a patient, the electrode assembly including an electrode adapted to capacitively couple treatment energy with the tissue to perform a non-invasive tissue treatment, said apparatus comprising:
   a handpiece adapted to removably receive the electrode assembly;
   an electrical circuit in said handpiece, said electrical circuit adapted to electrically couple the electrode with the energy-generating device; and
   at least one circuit element in said handpiece, said at least one circuit element configured to introduce at least one impedance into said electrical circuit when the electrode assembly is coupled with said handpiece, said at least one impedance being sized to reduce an impedance difference between a patient and a combination of the apparatus and the energy-generating device.

24. The apparatus of claim 23 wherein said at least one circuit element comprises at least one impedance element, said at least one impedance element selected from the group consisting of an inductor, a capacitor, a resistor, and combinations thereof.

25. The apparatus of claim 23 wherein said at least one circuit element comprises a variable inductor device, and the electrode assembly is configured to cooperate with said variable inductor device for changing an inductance of said variable inductor device to introduce said at least one impedance into said circuit.

26. The apparatus of claim 25 wherein said variable inductor device includes a first member and a second member movable relative to said first member in response to a stimulus from the electrode assembly for changing said inductance of said variable inductor device to provide different impedances.

27. The apparatus of claim 26 wherein said first member comprises a coil having a helical arrangement about an axis, and said second member comprises a core member formed from a magnetically permeable material, said core member movable along said axis between at least first and second positions relative to said coil in which said variable inductor device has different inductances.

28. The apparatus of claim 27 wherein said core member is movable between said first and second positions in response to a stimulus from the electrode assembly.

29. The apparatus of claim 23 wherein said at least one circuit element includes first and second impedance elements, and said electrical circuit includes a switch configured to be switched to add at least one of said first and second impedance elements into said electrical circuit.

30. The apparatus of claim 29 wherein said switch includes a first contact and a second contact movable relative to said first contact between a first position in which said first and second impedance elements are in said electrical circuit and a second position in which said second impedance element is in said electrical circuit.

31. The apparatus of claim 30 wherein said first contact is movable between said first and second positions in response to a stimulus from the electrode assembly.

32. The apparatus of claim 23 wherein said at least one circuit element includes first and second impedance elements of different impedances, and said electrical circuit includes a first electrical contact electrically coupling said first and second impedance elements in said electrical circuit and a second electrical contact electrically coupling said second impedance element in said electrical circuit.

33. The apparatus of claim 23 wherein said at least one circuit element comprises a digital memory device storing data relating to said at least one impedance, said digital memory device adapted to transfer said data to the energy-generating device so that the energy-generating device can introduce said at least one impedance to said electrical circuit.

34. The apparatus of claim 23 wherein said electrical circuit includes a switch configured to be switched between a first and second positions correlated with different impedances, said switch adapted to indicate to the energy-generating device which of said first and second positions is selected such that the energy-generating device can introduce said different impedances into said electrical circuit.

35. The apparatus of claim 34 wherein said switch includes a first electrical contact and a second electrical contact movable relative to said first electrical contact to provide said first and second positions.

36. The apparatus of claim 35 wherein said first contact is movable between said first and second positions in response to a stimulus from the electrode assembly.

37. A method of operating an energy-based medical system to treat tissue of a patient, the method comprising:
coupling a first electrode assembly in a handpiece to establish a first electrical circuit between an electrode in the first electrode assembly and an energy-generating device of the energy-based medical system, wherein the first electrode assembly has a first impedance;
introducing a second impedance into the electrical circuit that is related to the first impedance of the first electrode assembly; and
transferring energy from the first electrode assembly to the tissue,
wherein the second impedance is sized to reduce an impedance difference between a patient and a combination of the first electrode assembly and the energy-generating device.

38. The method of claim 37 further comprising:
removing the first electrode assembly from the handpiece;
coupling a second electrode assembly in the handpiece to establish a second electrical circuit between an electrode in the second electrode assembly and the energy-generating device, wherein the second electrode assembly has a different first impedance than the first electrode assembly;
selecting a different second impedance based upon at least one circuit element in the handpiece that is related to the different first impedance of the second electrode assembly;
introducing the different second impedance related to the different first impedance of the second electrode assembly into the second electrical circuit using at least one circuit element in the handpiece; and
transferring energy from the second electrode assembly to the tissue.

39. The method of claim 37 further comprising:
removing the first electrode assembly from the handpiece;
coupling a second electrode assembly in the handpiece to establish a second electrical circuit between an electrode in the second electrode assembly and the energy-generating device, wherein the second electrode assembly has a different first impedance than the first electrode assembly;
introducing a different second impedance related to the different first impedance of the second electrode assembly into the second electrical circuit using at least one circuit element in the second electrode assembly; and
transferring energy from the second electrode assembly to the tissue.

40. The method of claim 37 further comprising:
storing data representing the second impedance in a digital memory device in the electrode assembly; and
communicating the data to the energy-generating device when the first electrode assembly is coupled with the handpiece.

41. The method of claim 40 wherein introducing the second impedance into the electrical circuit further comprises:
introducing the second impedance into the electrical circuit with at least one circuit element associated with the energy-generating device.

42. The method of claim 37 wherein introducing the second impedance into the electrical circuit further comprises:
adjusting a variable inductor device when the first electrode assembly is coupled with the handpiece to provide the second impedance.

43. The method of claim 37 wherein introducing the second impedance into the electrical circuit further comprises:
  electrically coupling at least a first impedance element characterized by the second impedance in the electrical circuit.

44. The method of claim 43 wherein electrically coupling the at least a first impedance element further comprises:
  changing a position of a switch when the first electrode assembly is coupled with the handpiece to provide the second impedance.

45. The method of claim 37 wherein introducing the second impedance into the electrical circuit further comprises:
  providing the first electrode assembly with at least a first impedance element characterized by the second impedance and coupled with the electrical circuit when the first electrode assembly is coupled with the handpiece.

46. The method of claim 37 wherein introducing the second impedance into the electrical circuit further comprises:
  introducing the second impedance into the electrical circuit with at least one circuit element associated with the handpiece.

47. The method of claim 37 wherein introducing the second impedance into the electrical circuit further comprises:
  introducing the second impedance into the electrical circuit with at least one circuit element associated with the first electrode assembly.

* * * * *

UNITED STATES PATENT AND TRADEMARK OFFICE
CERTIFICATE OF CORRECTION

| | | |
|---|---|---|
| PATENT NO. | : 7,957,815 B2 | Page 1 of 1 |
| APPLICATION NO. | : 11/537155 | |
| DATED | : June 7, 2011 | |
| INVENTOR(S) | : Richard Wyeth et al. | |

It is certified that error appears in the above-identified patent and that said Letters Patent is hereby corrected as shown below:

In the Specification:

At column 8, line number 53, change "element elements" to --elements--.

At column 9, line number 31, after "48", insert --to--.

At column 13, line number 8, change "in" to --is--.

In the Claims:

At column 17, claim number 34, line number 58, after "between", insert --a--.

Signed and Sealed this
Sixteenth Day of August, 2011

David J. Kappos
*Director of the United States Patent and Trademark Office*